United States Patent
Sternby

(10) Patent No.: US 10,625,013 B2
(45) Date of Patent: Apr. 21, 2020

(54) DETECTION OF A DISRUPTION OF A FLUID CONNECTION BETWEEN TWO FLUID CONTAINING SYSTEMS

(71) Applicant: GAMBRO LUNDIA AB, Lund (SE)

(72) Inventor: Jan Sternby, Lund (SE)

(73) Assignee: GAMBRO LUNDIA AB, Lund (SE)

(*) Notice: Subject to any disclaimer, the term of this patent is extended or adjusted under 35 U.S.C. 154(b) by 0 days.

(21) Appl. No.: 16/312,142

(22) PCT Filed: May 8, 2017

(86) PCT No.: PCT/EP2017/060902
§ 371 (c)(1),
(2) Date: Dec. 20, 2018

(87) PCT Pub. No.: WO2018/001610
PCT Pub. Date: Jan. 4, 2018

(65) Prior Publication Data
US 2019/0240392 A1    Aug. 8, 2019

(30) Foreign Application Priority Data
Jun. 30, 2016 (SE) .......... 1650945

(51) Int. Cl.
*G01F 23/24* (2006.01)
*A61M 1/36* (2006.01)
*G16H 20/40* (2018.01)

(52) U.S. Cl.
CPC .......... *A61M 1/3656* (2014.02); *G16H 20/40* (2018.01); *A61M 2205/14* (2013.01);
(Continued)

(58) Field of Classification Search
CPC . A61B 3/102; A61M 1/3656; A61M 2205/18; A61M 2205/3331;
(Continued)

(56) References Cited

U.S. PATENT DOCUMENTS 6,090,048 A    7/2000   Hertz et al.
6,663,585 B1  12/2003   Ender
(Continued)

FOREIGN PATENT DOCUMENTS

JP    2010136745    6/2010
WO       0147581    7/2001
(Continued)

OTHER PUBLICATIONS

International Search Report and Written Opinion for International Application No. PCT/EP2017/060902, dated Sep. 6, 2017; (11 pages).

*Primary Examiner* — Daniel Previl
(74) *Attorney, Agent, or Firm* — K&L Gates LLP

(57) ABSTRACT

A monitoring device is operated to detect a disruption of a fluid connection between two fluid containing systems. A disruption detector in the monitoring device operates on a measurement signal (Pi) to detect an apparent disruption of the fluid connection and generate a corresponding alarm indication. The monitoring device is configured to optimize the configuration of the disruption detector to limit the number of false alarms, by operating a false alarm analyzer to produce a count (FA #) of false alarm indications generated per unit time by the disruption detector for one or more configurations (ΔL) of the disruption detector, and by operating an updater to update the configuration (ΔL) of the disruption detector based on the count (FA #). The monitoring device may be connected to or part of an apparatus for blood treatment and operable to detect a disconnection of an extracorporeal blood circuit from a vascular system of a patient, e.g. a venous-side disconnection.

21 Claims, 5 Drawing Sheets

(52) U.S. Cl.
CPC . *A61M 2205/18* (2013.01); *A61M 2205/3317* (2013.01); *A61M 2205/3327* (2013.01); *A61M 2205/3331* (2013.01); *A61M 2205/3344* (2013.01); *A61M 2205/50* (2013.01); *A61M 2205/702* (2013.01); *A61M 2230/04* (2013.01)

(58) Field of Classification Search
CPC .......... A61M 2205/50; A61M 2205/14; A61M 2205/3317; A61M 2205/3327; A61M 2205/3344; A61M 2205/702; A61M 2230/04; A61M 2205/15; A61M 2230/06; G06T 2207/10101; G06T 2207/20156; G06T 7/11; G06T 7/187; G06T 2207/20141; G06T 7/0081; G01B 11/026; G01B 11/14; G01B 2290/30; G01B 2290/45; G01B 2290/70; G01B 9/02061; G01B 9/02081; G01K 11/32; G10K 11/16; G10K 11/17819; G10K 11/17833; G10K 11/17881; G10K 11/17885; G10K 2210/108; G10K 2210/3023; G10K 2210/3055; G10K 2210/503; G10K 2210/505; G10K 2210/506; G16H 20/40; G01F 1/662; G01F 1/667; G01N 15/0266; G01N 15/1031; G01N 2015/0096; G01N 2015/1075; G01N 22/04; G01P 5/248; G01R 23/00; G01S 13/92; H03G 3/3005; H04L 41/0826; H04L 41/083; H04L 65/403; H04L 67/1051; H04L 67/38; H04N 21/632
USPC ...... 340/603, 618, 624, 636.11–636.18, 657, 340/5.74, 825.36, 7.22, 7.51, 286.07
See application file for complete search history.

(56) References Cited

U.S. PATENT DOCUMENTS

| | | | | |
|---|---|---|---|---|
| 7,575,562 | B2* | 8/2009 | Oishi | A61B 5/02152 604/4.01 |
| 2003/0194894 | A1* | 10/2003 | Wariar | A61M 1/3656 439/191 |
| 2003/0195453 | A1* | 10/2003 | Han | A61M 1/3653 604/5.01 |
| 2003/0195454 | A1* | 10/2003 | Wariar | A61M 1/3653 604/5.01 |
| 2005/0010118 | A1 | 1/2005 | Toyoda et al. | |
| 2007/0000847 | A1* | 1/2007 | Ross | A61M 1/3621 210/781 |
| 2009/0292236 | A1 | 11/2009 | Kleinekofort | |
| 2011/0034814 | A1 | 2/2011 | Kopperschmidt | |
| 2015/0306301 | A1 | 10/2015 | Strohhoefer et al. | |

FOREIGN PATENT DOCUMENTS

| | | |
|---|---|---|
| WO | 2009045582 | 4/2009 |
| WO | 2009122229 | 10/2009 |
| WO | 2009156174 | 12/2009 |
| WO | 2009156175 | 12/2009 |
| WO | 2010149726 | 12/2010 |
| WO | 2011080193 | 7/2011 |
| WO | 2012175267 | 12/2012 |
| WO | 2013000777 | 1/2013 |
| WO | 2014009111 | 1/2014 |
| WO | 2014095524 | 6/2014 |
| WO | 2014107656 | 7/2014 |
| WO | 2015049056 | 4/2015 |

* cited by examiner

DETECTION OF A DISRUPTION OF A FLUID CONNECTION BETWEEN TWO FLUID CONTAINING SYSTEMS

PRIORITY CLAIM

The present application is a National Phase of International Application No. PCT/EP2017/060902, filed May 8, 2017, which claims priority to Swedish Patent Application No. 1650945-7, filed Jun. 30, 2016, the entire contents of each of which are incorporated herein by reference and relied upon.

TECHNICAL FIELD

The present invention relates to a technique for detecting a disruption of a fluid connection between two fluid containing systems, based on at least one measurement signal generated by a sensor arranged in or associated with one of the fluid containing systems. The fluid connection may be established between an extracorporeal circuit for blood processing and the vascular system of a human subject.

BACKGROUND ART

In extracorporeal blood processing, blood is taken out of a human subject, processed (e.g. treated) and then reintroduced into the subject by means of an extracorporeal blood flow circuit ("EC circuit") which is part of a system or machine for blood processing. Generally, the blood is circulated through the EC circuit by a blood pump. In certain types of extracorporeal blood processing, the EC circuit includes an access device for blood withdrawal (e.g. an arterial needle or catheter) and an access device for blood reintroduction (e.g. a venous needle or catheter), which are inserted into a dedicated blood vessel access (e.g. fistula, graft or catheter) on the subject. The access devices form a fluid connection between the EC circuit and the cardiovascular system of the subject. This type of EC circuit is, e.g., used in extracorporeal blood treatments such as hemodialysis, hemodiafiltration, hemofiltration, plasmapheresis, bloodbanking, blood fraction separation (e.g. cells) of donor blood, apheresis, extracorporeal blood oxygenation, assisted blood circulation, extracorporeal liver support/dialysis, ultrafiltration, heart congestion failure treatment, etc.

It is vital to minimize the risk for malfunctions in the fluid connection that may lead to a potentially life-threatening condition of the subject. A particularly serious condition may arise if the EC circuit is disrupted downstream of the blood pump while the blood pump is running, e.g. by the access device for blood reintroduction coming loose from the blood vessel access. Such a venous-side disruption, which is commonly referred to as a Venous Needle Dislodgement (VND), may cause the subject to be drained of blood within minutes. A disruption on the arterial side, e.g. by the access device for blood withdrawal coming loose from the blood vessel access, may also present a patient risk, by air being sucked into the EC circuit and transported into the cardiovascular system, causing air embolism.

Machines for extracorporeal blood treatment typically include a safety system that monitors the status of the fluid connection between the EC circuit and the subject and triggers an alarm and/or an appropriate safety action whenever a potentially dangerous situation is detected. In dialysis machines, it is common for such safety systems to operate on a pressure signal from a pressure sensor in the EC circuit, where the fluid pressure measured by the pressure sensor is responsive to a disconnection of the EC circuit from the blood vessel access. For example, the pressure sensor may be arranged to measure the pressure level on the venous side of the EC circuit. A venous-side disconnection results in a changed venous-side pressure, which may be detected by comparing the measured pressure level with one or more alarm thresholds that define a predefined, allowable pressure range.

Conventionally, the alarm thresholds are set, automatically by the machine or manually by an operator, and subsequently acknowledged by the operator at the beginning of a treatment session and may remain fixed throughout the session. The machine may allow the operator to manually change the alarm thresholds, and the machine may automatically change the alarm thresholds when the blood flow in the EC circuit is changed.

Generally, the alarm thresholds are primarily set to avoid false negatives in the VND detection, i.e. missed alarm conditions, and thus inevitably results in generation of false positives, i.e. false alarms. At the same time, it is important to avoid frequent false alarms that require the attention of dialysis personnel. A difficulty in this context is that the measured pressure level may change for other reasons than a VND during a treatment session, e.g. as a result of the patient moving, variations in the blood flow rate through the EC circuit, variations in the pressure drop in the access devices, variations in the composition of the blood (e.g. hematocrit), wear in the blood pump, changes in access pressure, etc.

It may be equally challenging to set alarm thresholds in other techniques that are used or proposed for monitoring of the status of the fluid connection between the EC circuit and the subject. Such other techniques may involve detecting pressure waves that have propagated via the fluid connection to a pressure sensor in the EC circuit, applying a blood leakage sensor onto the vascular access to detect presence of wetness or blood, operating an optical sensor attached to the patient to detect a perturbation transmitted from the apparatus to the patient via the fluid connection, analyzing an image signal from a camera directed to the vascular access, electrically detecting a disconnection of the access device from the vascular access, etc.

Although the foregoing description is given in the context of extracorporeal blood processing, it is understood that a corresponding need to detect a disruption of a fluid connection between two fluid containing systems may arise in other fields of technology.

SUMMARY

It is an objective of the invention to at least partly overcome one or more of limitations of the prior art.

Another objective is to provide an improved monitoring technique for detecting a disruption of a fluid connection between two fluid containing systems.

Yet another objective is to provide such a monitoring technique that reduces the risk for false positives without increasing the risk for false negatives.

A still further objective is to provide such a monitoring technique which is robust and simple to implement.

A further objective is to provide such a monitoring technique which is applicable for detecting a return-side disconnection of an extracorporeal blood circuit from the vascular system of a subject.

One or more of these objectives, as well as further objectives that may appear from the description below, are at least partly achieved by a monitoring device, an apparatus for extracorporeal blood processing, a method of controlling a monitoring device, and a computer-readable medium according to the independent claims, embodiments thereof being defined by the dependent claims.

A first aspect of the invention is a monitoring device. The monitoring device comprises a disruption detector configured to obtain a measurement signal, which is generated by a sensor arranged in or associated with a first fluid containing system and is responsive to a disruption of a fluid connection between the first fluid containing system and a second fluid containing system. The disruption detector is further configured to operate on the measurement signal to detect an apparent disruption of the fluid connection and generate an alarm indication corresponding to the apparent disruption. The monitoring device further comprises an alarm module for activating an alarm based on the alarm indication, a false alarm analyzer configured to produce a count of false alarm indications generated per unit time by the disruption detector for one or more configurations of the disruption detector, and an updater configured to update the configuration of the disruption detector based on the count.

The first aspect presumes that the disruption detector is reconfigurable, i.e. capable of being set to operate in different configurations, and is based on the insight that it is possible to improve existing monitoring techniques that operate a disruption detector on a measurement signal to detect an apparent disruption of a fluid connection by updating the configuration of the disruption detector to produce no more than a desired number of false alarms per unit time. Thus, the respective update may, but need not, result in a change of configuration of the disruption detector. The update may be effected as part of a start-up procedure of the monitoring device, so as to prepare the monitoring device for operation as a safety system. Alternatively or additionally, the update is effected intermittently, e.g. during or throughout the operation of the monitoring device as a safety system. The update is effected based on a count of the number of false alarms produced by the disruption detector, in one or more configurations, for the measurement signal. Thus, one or more configurations of the disruption detector is assessed in relation to the actual measurement signal that is used for monitoring, which ensures that the update may effectively improve the performance of the disruption detector, by reducing the risk for false positives without increasing the risk for false negatives.

The first aspect is simple to implement since it requires no fundamental redesign of the disruption detector itself. Given that the disruption detector is reconfigurable, the first aspect is achieved by merely providing an appropriate false alarm analyzer and an appropriate updater, which are straight-forward modules that may be implemented by simple software routines and/or hardware devices. Thus, the first aspect may be implemented to improve any existing or future monitoring technique for detecting a disruption of a fluid connection, including monitoring techniques for detecting a return-side disconnection of an extracorporeal blood circuit from a vascular system of a subject.

In one embodiment, the disruption detector is configured to, when operating on the measurement signal, generate a time-sequence of parameter values of a detection parameter to represent a time segment in the measurement signal, compare the time-sequence of parameter values to a current allowable range, and generate the alarm indication when a predefined number of parameter values in the time-sequence of parameter values fall outside the current allowable range. Further, the updater may be configured to update the configuration of the disruption detector by one or more of: causing the disruption detector to operate on another measurement signal, causing the disruption detector to modify a preprocessing of the measurement signal, causing the disruption detector to generate the time-sequence of parameter values of another detection parameter, changing the current allowable range, and changing the predefined number of parameter values.

The first aspect may be implemented in two different ways, denoted first and second implementation concepts in the following.

According to the first implementation concept, the false alarm analyzer is configured to produce the count to represent the number of false alarm indications among the alarm indications that are generated by the disruption detector over a time period. The first implementation concept thus uses the actual behavior of the disruption detector to update its configuration. The first implementation concept is simple and straight-forward to implement, since it merely involves counting the number of false alarms that are generated during operation the disruption detector, and taking action based on the count. It is conceivable that each false alarm is identified as such to the false alarm analyzer by an operator of the monitoring device, e.g. by the operator assessing whether each alarm indication corresponds to an actual alarm situation or not and signaling each false alarm to the monitoring device. However, the monitoring device is preferably configured to automatically and autonomously identify false alarms among the alarm indications generated by the disruption detector.

In one embodiment of the first implementation concept, the updater is configured to update the configuration of the disruption detector by increasing or decreasing the current allowable range as a function of the count. Further, the updater may be configured to update the configuration of the disruption detector by repeatedly increasing or decreasing the current allowable range until the count meets a desired value.

According to the second implementation concept, the false alarm analyzer is configured to produce the count by estimating, based on the measurement signal, a respective number of false alarm indications generated by the disruption detector for each of a plurality of different configurations of the disruption detector. The second implementation concept thus involves a hypothetical evaluation of the number of false alarms produced by the disruption detector in a number of different configurations. Thus, in the second implementation concept, the disruption detector is not actually set in the different configurations, but the evaluation is made by analyzing the number of false alarms that would have been generated if the disruption detector would have been set in the respective configuration. By jointly analyzing a plurality of hypothetical configurations of the disruption detector, the second implementation concept is capable of quickly setting the disruption detector to a configuration that yields a desired number of false alarms per unit time. Compared to the first implementation concept, the second implementation concept involves a slightly higher computational cost.

In one embodiment of the second implementation concept, the false alarm analyzer is configured to compare at least part of the time-sequence of parameter values to each allowable range among a plurality of allowable ranges, identify a respective false alarm indication when a set of parameter values in the time-sequence of parameter values falls outside the respective allowable range, and produce the count to represent the number of false alarm indications for the respective allowable range. Further, the updater may be configured to set the current allowable range as a function of the allowable range for which the count meets a desired value.

Further embodiments of the monitoring device are defined below and may serve the purpose of reducing the number of false positives, improving robustness, facilitating implementation, or another purpose as understood by the skilled person.

In one embodiment, the disruption detector is further configured to, when operating on the measurement signal, perform an automatic validation of each alarm indication to identify the alarm indication as a false alarm indication or a true alarm indication, wherein the false alarm analyzer is configured to produce the count based on the false alarm indications identified by the automatic validation. Further, the automatic validation may involve one or more of: obtaining and processing a further measurement signal generated by a further sensor arranged in or associated with the first or second fluid containing systems and being responsive to the disruption; generating parameter values of another detection parameter as a function of the measurement signal; and intermittently disabling one or more sources of signal interferences in the measurement signal.

In one implementation, the first fluid containing system comprises a blood processing apparatus for connection, by the fluid connection, to a subject, wherein the sensor comprises a pressure sensor for sensing a pressure of blood in the blood processing apparatus, wherein the automatic validation comprises: obtaining and processing the measurement signal for detection of pulsations originating from a pulse generator in or associated with the subject. In this implementation, the automatic validation may further comprise, before obtaining and processing the measurement signal, generating a control signal to stop one or more pumping devices arranged in the blood processing apparatus.

In one embodiment, the alarm module is configured to activate the alarm signal when the automatic validation identifies the alarm indication as a true alarm indication.

In one embodiment, the updater is configured to update the configuration of the disruption detector at fixed time intervals and/or triggered by the count.

In one embodiment, the measurement signal represents fluid pressure in the first fluid containing system, and the parameter values are indicative of one of a pressure level in the first fluid containing system, and pulsations originating from a pulse generator in the second fluid containing system.

A second aspect of the invention is an apparatus for extracorporeal blood processing. The apparatus comprises an extracorporeal blood circuit for connection in fluid communication with the vascular system of a patient at first and second ends and comprising a blood pump for circulating blood from the first end through a blood processing device to the second end; a sensor configured to generate a measurement signal which is responsive to a disconnection of the extracorporeal blood circuit from the vascular system of the patient downstream of the blood pump; a disconnection detector configured to operate on the measurement signal for detecting the disconnection and generate an alarm indication corresponding to the disconnection; and an alarm module for activating an alarm based on the alarm indication. The apparatus further comprises a false alarm analyzer configured to produce a count of false alarm indications generated by the disconnection detector per unit time for one or more configurations of the disconnection detector; and an updater configured to intermittently update the configuration of the disconnection detector based on the count.

A third aspect of the invention is a method of controlling a monitoring device comprising a processor. The method is executed by the processor in the monitoring device and comprises: obtaining a measurement signal generated by a sensor in a first fluid containing system and being responsive to disruptions of a fluid connection between the first fluid containing system and a second fluid containing system; operating a detection logic on the measurement signal to detect an apparent disruption of the fluid connection and generate an alarm indication corresponding to the apparent disruption; activating an alarm based on the alarm indication; and intermittently updating the detection logic based on a count of false alarm indications per unit time among the alarm indications generated by the detection logic for one or more configurations of the detection logic.

In one embodiment, which corresponds to the above-mentioned first implementation concept, the method further comprises: producing the count to represent the number of false alarm indications per unit time among the alarm indications that are generated when operating the detection logic, in a current configuration, on the measurement signal.

In another embodiment, which corresponds to the above-mentioned second implementation concept, the method further comprises: estimating, based on the measurement signal, the number of false alarm indications generated by the detection logic for each of a plurality of different configurations of the detection logic, and producing the count to represent the number of false alarm indications for each of the plurality of different configurations.

A fourth aspect of the invention is a computer-readable medium comprising processing instructions for causing a data processor to perform the method of the third aspect.

Any one of the above-identified embodiments of the first aspect may be adapted and implemented as an embodiment of the second to fourth aspects.

Still other objectives, features, aspects and advantages of the present invention will appear from the following detailed description, from the attached claims as well as from the drawings.

DETAILED DESCRIPTION OF EXAMPLE EMBODIMENTS

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more," even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Figure 1:
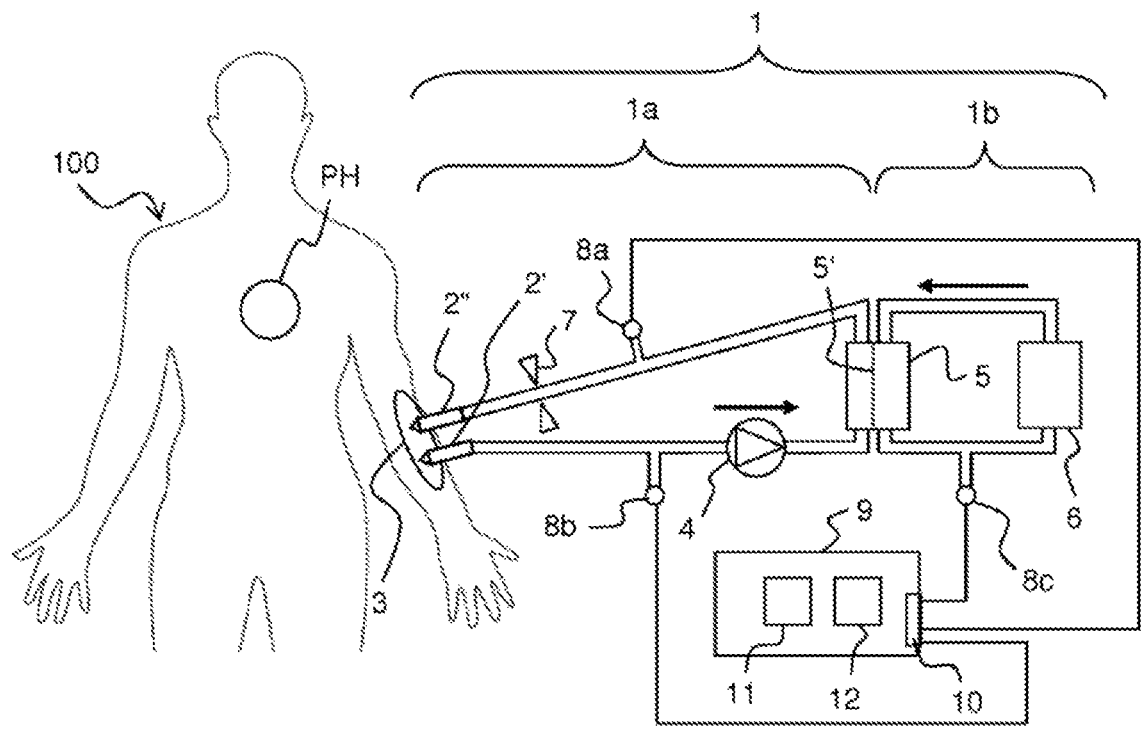
FIG. 1 is a schematic diagram of an extracorporeal blood processing apparatus attached to a human subject and comprising a monitoring device for disconnection detection.

Embodiments of the invention will be exemplified with reference to an apparatus 1 for blood treatment, which is schematically depicted in FIG. 1. In the following example, the apparatus 1 is assumed to be a dialysis system which is formed by a blood line set attached to a dialysis machine or monitor, as is well known in the art. FIG. 1 illustrates a human subject or patient 100 which is connected to an extracorporeal blood flow circuit 1a by way of access devices 2', 2" inserted into a dedicated vascular access 3 (also known as "blood vessel access") on the patient. The extracorporeal blood flow circuit 1a (denoted "EC circuit" in the following) is configured to communicate blood to and from the cardiovascular system of the patient. In the illustrated example, a blood pump 4 is operable to draw blood from the vascular access 3 via an access device 2' for blood withdrawal and to pump the blood through a blood treatment unit 5 and back to the vascular access 3 via an access device 2" for blood return. Thus, when both access devices 2', 2" are connected to the vascular access 3, the EC circuit 1a defines a blood path that starts and ends at the vascular access 3. The EC circuit 1a may be seen to comprise a "venous side" which is the part of the blood path located downstream of the blood pump 4, and an "arterial side" which is the part of the blood path located upstream of the blood pump 4. The blood pump 4 may be of any type, e.g. a rotary peristaltic pump, a linear peristaltic pump, a diaphragm pump, or a centrifugal pump.

The blood treatment unit 5 may be any type of blood filtration device, such as a coil dialyzer, a parallel plate dialyzer, a hollow fiber dialyzer, etc. For simplicity, the blood treatment unit 5 is denoted "dialyzer" in the following. The dialyzer 5 has a blood side and a treatment fluid side separated by a semipermeable membrane 5'. The blood side is connected as part of the EC circuit 1a, and the treatment fluid side is connected as part of a supply system 1b for treatment fluid (denoted "TF circuit" in the following). The TF circuit 1b is arranged to pump a treatment fluid through the treatment fluid side of the dialyzer 5, whereby solutes are transported over the membrane 5' due to a concentration gradient and/or ultrafiltrate is transported over the membrane 5' due to a pressure gradient. The skilled person understands that the TF circuit 1b may include a plurality of functional components such as a source of fresh treatment fluid, a receptacle/drain for spent treatment fluid, one or more pumps, balancing chambers, valves, heaters, conductivity sensors, etc. For simplicity, these components are collectively represented by a generic box 6 in FIG. 1.

In the example of FIG. 1, a clamp 7 is arranged on the venous side of the EC-circuit 1a. Although not shown, a corresponding clamp may be arranged on the arterial side. The clamp(s) 7 may be operated to block fluid passage through the blood lines, e.g. before and after a treatment session, or as part of the apparatus entering a safe state following detection of an alarm condition.

It is understood that the EC circuit 1a and the TF circuit 1b form part of the above-mentioned apparatus 1 for blood treatment. A main control unit (not shown) in the apparatus 1 may control and synchronize the operation of, e.g., the blood pump 4, the components 6, the clamp(s) 7, as well as further components such as pumps, sensors, valves, a user interface, etc.

The EC circuit 1a includes a pressure sensor or transducer 8a (denoted "venous pressure sensor" or "venous sensor") on the venous side of the EC circuit 1a, downstream of the dialyzer 5, a pressure sensor or transducer 8b (denoted "arterial pressure sensor" or "arterial sensor") on the arterial side of the EC circuit 1a. The venous and arterial sensors 8a, 8b provide a respective time-varying signal that represents the pressure in the blood on the venous side ("venous signal") and the arterial side ("arterial signal"), respectively. In the example of FIG. 1, a pressure sensor or transducer 8c (denoted "TF pressure sensor" or "TF sensor") is also arranged in the TF circuit 1b to provide a time-varying signal that represents the pressure in the treatment fluid. The TF sensor 8c may have any placement in the TF circuit 1b, e.g. downstream (as in FIG. 1) or upstream of the dialyzer 5.

Generally, the EC circuit 1a and the TF circuit 1b may be seen to define a fluid containing system, which is connected to another fluid containing system constituted by the cardiovascular system of the patient 100. A monitoring device 9 is arranged to detect a disruption of a fluid connection between the fluid containing systems, typically during ongoing blood treatment. When detecting a (potential) malfunction, the device 9 may issue an alarm or warning signal to alert an operator of the apparatus 1 and/or cause the main control unit of the apparatus 1 to take appropriate action. The device 9 may be included as part of the apparatus 1 for blood treatment, and may be connected to or part of the above-mentioned main control unit. Alternatively, the device 9 is separate from the apparatus 1.

Depending on implementation, the monitoring device 9 may be configured to detect a disruption occurring on the venous side of the EC circuit 1a and/or on the arterial side of the EC circuit 1a. The disruption may correspond to a disconnection of the EC circuit 1a from the cardiovascular system and may be caused, e.g., by a dislodgement of the respective access device 2', 2" from the vascular access 3, a rupture of a blood line in the EC circuit 1a, or a disconnection of a connector (not shown) which may be installed between the respective access device 2', 2" and the blood line. Techniques for detecting a disconnection on the venous-side of the EC circuit 1a are denoted "VND techniques" herein. Additionally or alternatively, the monitoring device 9 may be configured to detect a disruption caused by other malfunctions of the EC circuit 1a, e.g. that a blood line is kinked, or that the respective access device 2', 2" is positioned too close to, or inserted into, a wall of the blood vessel access 3 (known as "infiltration").

The monitoring device 9 comprises a signal interface 10 for receiving measurement signal(s) from one or more appropriate sensors, and processing circuitry 11, 12 for processing the measurement signal(s) for the purpose of detecting the disruption of the fluid connection. In the example of FIG. 1, the monitoring device is connected to receive and process the pressure signals from the pressure sensors 8a, 8b, 8c for disruption detection. However, it should be noted that the monitoring device 9 may be implemented to utilize any available technique or combination of techniques for detecting a disruption. Thus, the monitoring device 9 may operate on any number of measurement signals from any type of sensors, provided that at least one of the measurement signals is responsive to the disruption to be detected. As used herein, "responsive to" indicates that the disruption results in a change in the measurement signal. For example, such a measurement signal may be a pressure signal from a pressure sensor in the apparatus, a signal from a blood leakage sensor attached onto the vascular access to detect presence of wetness or blood, a signal from an optical sensor attached to the patient to detect a perturbation transmitted from the apparatus to the patient via the fluid connection, a signal from an electrical disconnection sensor, an image signal from a camera directed to the vascular access, etc. The signal from the optical sensor may e.g. be processed for disruption detection in accordance with WO2009/122229. The electrical disconnection sensor may be configured to measure electrical current, voltage, capacitance, or an equivalent quantity, e.g. as disclosed in any one of WO01/47581, U.S. Pat. No. 6,663,585, US2003/0194894, US2003/0195453, US2003/0195454 and US2007/0000847.

As will be explained in further detail below, embodiments of the monitoring device 9 are configured to intermittently update a detection logic, which controls the disruption detection in the monitoring device 9, based on an estimated or actual count of false alarm indications generated by the monitoring device for a time segment in the measurement signal(s).

Embodiments of the invention may e.g. be at least partly implemented by software instructions that are supplied on a computer-readable medium for execution by a processor 11 in conjunction with an electronic memory 12 in the device 9.

Figure 2:
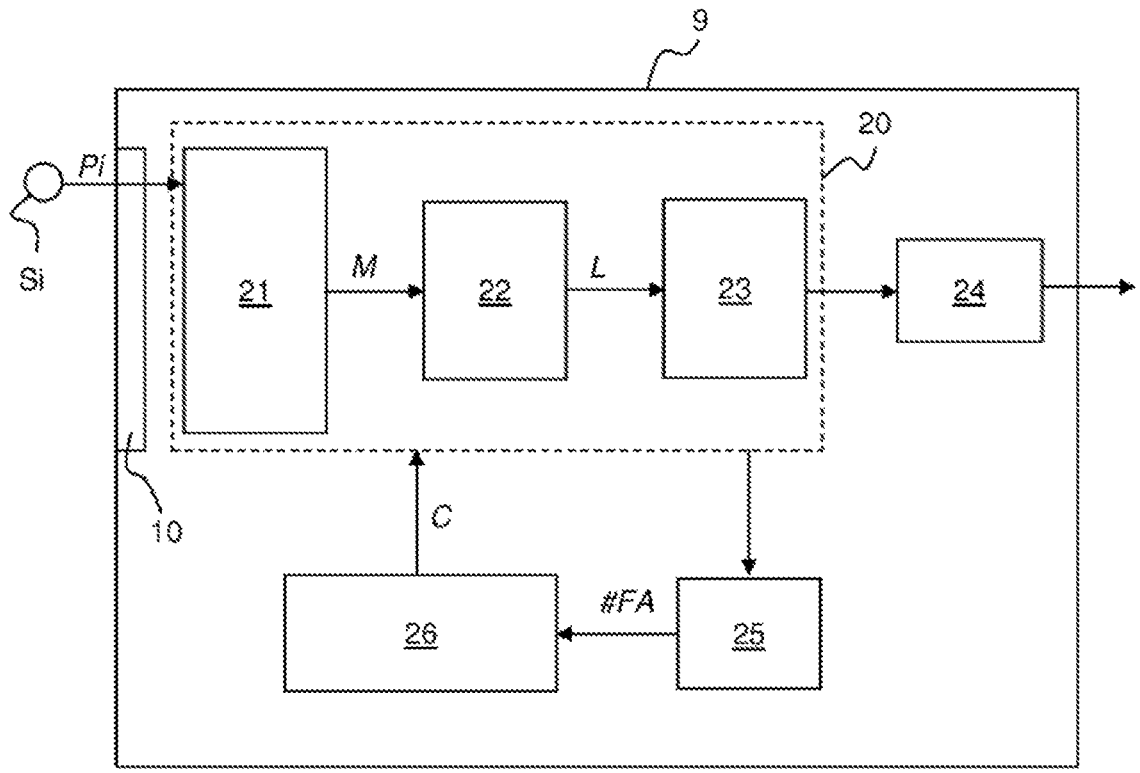
FIG. 2 is a block diagram of a monitoring device according to an embodiment.

FIG. 2 illustrates an embodiment of the monitoring device 9 for disruption detection. The device 9 is connected by the signal interface 10 to a sensor Si to receive a measurement signal Pi which is responsive to the disruption to be detected. The sensor Si may be any one of the sensors discussed in the foregoing. The device 9 comprises modules or blocks that implement a respective functionality. The respective module may be implemented by hardware circuitry, by software executed by the processor 11, or by a combination of hardware circuitry and software.

The device 9 comprises a disruption detection module 20 ("disruption detector") which is configured to operate a detection logic on the measurement signal Pi to detect an apparent disruption of the fluid connection and generate an alarm indication corresponding to the apparent disruption. As used herein, "detection logic" is a definition of the configuration of the disruption detector 20 and the steps to be executed for processing the measurement signal Pi and for deciding if there is an apparent disruption of the fluid connection.

In the example of FIG. 2, the disruption detector 20 comprises a preprocessing sub-module 21 ("preprocessor") which is configured to generate a time-varying monitoring signal M based on the time-varying measurement signal Pi. The preprocessor 21 may be configured to process the measurement signal Pi by, e.g., AD conversion, signal amplification, and removal of offset, high frequency noise and supply voltage disturbances. The preprocessor 21 may also process the measurement signal Pi by any known signal filtering technique for suppression of signal artefacts that originate from the apparatus 1 and/or the patient 100. For example, a measurement signal Pi that is generated by a pressure sensor in the apparatus 1 may contain strong signal artefacts ("pump pulses") that originate from the blood pump 4, as well as signal artefacts that originate from the TF circuit 1b, e.g. from balancing chambers, pumps, valves, etc. Examples of such signal filtering techniques are found in WO2009/156175, WO2010/149726, WO2013/000777, WO2014/009111 and WO2014/095524. It should be noted that the preprocessor 21 may be configured to generate the monitoring signal M based on a combination of (filtered) measurement signals, e.g. as a (weighted) difference or sum of two signals.

The disruption detector 20 further comprises a parameter computation sub-module 22 ("extractor"), which is configured to process the time-varying monitoring signal M for generation of parameter values of at least one detection parameter. The parameter extractor 22 thereby produces a time-sequence of parameter values L that represent or correspond to a time segment in the measurement signal.

Figure 3:
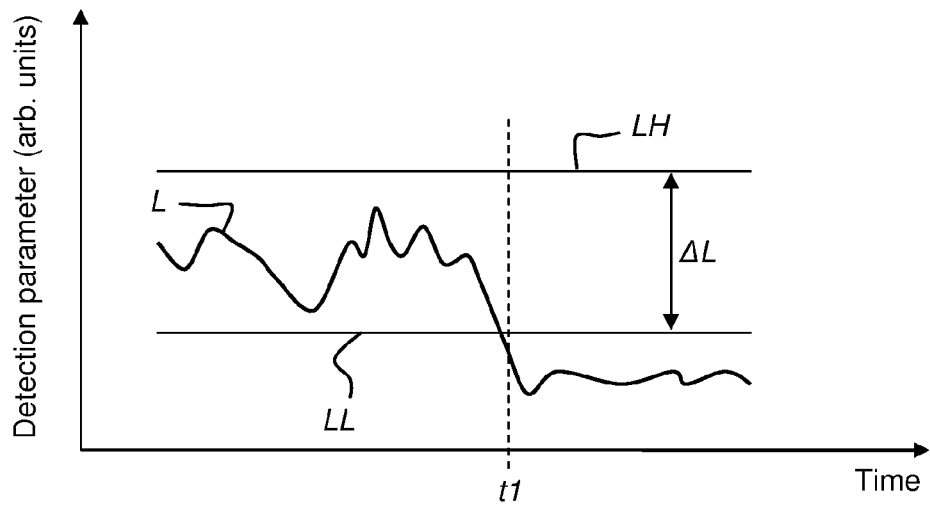
FIG. 3 is a plot of parameter values extracted from a measurement signal and compared to a current allowable range.

The disruption detector 20 further comprises a parameter analysis sub-module 23 ("analyzer"), which is configured to process the time-sequence of parameter values L for detection of a possible disruption. In one embodiment, further illustrated in FIG. 3, the analyzer 23 is configured to compare the time-sequence of parameter values L to an allowable range ΔL and generate an alarm indication when an alarm criterion is fulfilled. For example, the alarm criterion may be fulfilled when a predefined number of parameter values L (either consecutive or during a given time period) are found to fall outside the allowable range ΔL. The predefined number may be any positive number. In FIG. 3, the alarm indication is generated at time t1. In FIG. 3, the range ΔL is defined between two limits LL, LH. In an alternative, the range ΔL is defined by a single limit, so as to include all parameter values above or below this single limit.

The monitoring device 9 of FIG. 2 further comprises an alarm module 24, which is configured to generate an alarm signal based on alarm indications generated by the disruption detector 20. The alarm signal may activate an alarm in the form of an audible and/or visible signal or message to alert a caretaker of a malfunction of the apparatus 1. The alarm signal may also cause the main control unit of the apparatus 1 to enter a safe state, e.g. by closing the clamp 7 and stopping the blood pump 4.

The monitoring device 9 further comprises a false alarm analysis module 25 ("FA analyzer"), which is configured to produce a count # FA of false alarm indications generated per unit time for one or more configurations of the disruption detector 20. Different implementations of the FA analyzer 25 are conceivable. In a first implementation concept, which will be further described in relation to FIGS. 5A-5B, the FA analyzer 25 produces the count # FA based on actual false alarms generated by the disruption detector 20 when operating on the measurement signal, i.e. for a current detection logic. In the first implementation concept, the monitoring device 9 is preferably configured to autonomously identify false alarms among the alarm indications produced by the disruption detector 20 and to hide the false alarms from the user, at least to the extent that no alarm signal is generated for the false alarms. In a second implementation concept, which will be further described in relation to FIGS. 6A-6B, the FA analyzer 25 evaluates the number of false alarms that would have been generated for each of a plurality of different configurations of the detection logic, when operated on a time segment in the measurement signal. Thus, in the second implementation concept, the count # FA is produced by operating a number of hypothetical variants of the disruption detector 20 on a time segment in the measurement signal to assess the resulting number of false alarms for each hypothetical variant. Thereby, the FA analyzer 25 produces one count # FA for each hypothetical variant.

In both implementation concepts, the FA analyzer 25 may be configured to produce the count # FA to include one false alarm indication for each coherent time period in which the alarm criterion is fulfilled and the fluid connection is not disrupted. In the example of FIG. 3, assuming that the drop in parameter values L is not caused by a disruption, one false alarm indication would be identified, at time t1. Thus, the count # FA is generated to represent the number of intermittent time periods with an incorrectly (falsely) fulfilled alarm condition. In an alternative, the FA analyzer 25 is instead configured to produce the count # FA to include false alarm indications for all time steps within each of the above-mentioned coherent time periods. In the example of FIG. 3, false alarm indications would be identified for all time steps from time t1 until the alarm condition is no longer fulfilled. Thus, in this alternative, the count # FA is effectively generated to represent the total length of the coherent time periods with an incorrectly fulfilled alarm condition.

The monitoring device 9 further comprises an updating module 26 ("updater"), which is configured to intermittently generate a control signal C for updating the detection logic, i.e. the configuration of the disruption detector 20, based on the count # FA produced by the FA analyzer 25. The control signal C may be generated to update one or more of the sub-modules 21-23 of the disruption detector 20. The update may involve invoking a particular process in a sub-module or changing one or more operating parameters of a particular process in a sub-module. For example, the preprocessor 21 may be updated to change the measurement signal(s) to be preprocessed (provided that the signal interface 10 is connected to receive more than one measurement signal), to select another signal filtering technique for suppression of signal artefacts, to activate/deactivate signal filtering for suppression of signal artefacts, and to change the number of measurement signals to be combined into the monitoring signal and/or the logic for combining the measurement signals. The extractor 22 may be updated to change the detection parameter, e.g. by switching to another algorithm for computing the respective parameter value based on the monitoring signal M, or by changing the number of signal values in the monitoring signal M to be processed for generating each parameter value. The analyzer 23 may be updated to change the allowable range ΔL, or to change a criterion for generating an alarm indication, such as the number of parameter values L that should fall outside the allowable range ΔL.

Figure 4:
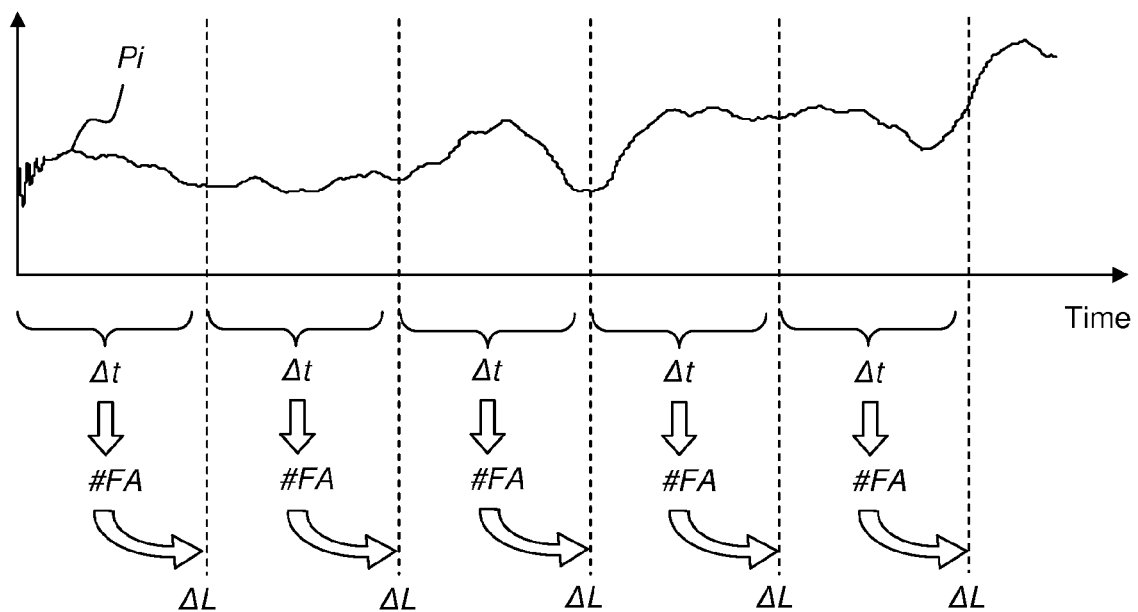
FIG. 4 illustrates an updating functionality of the monitoring device in relation to a measurement signal generated in the apparatus of FIG. 1.

The updater 26 may be triggered to generate the control signal C at fixed time intervals. Alternatively or additionally, the updater 26 may be triggered to generate the control signal C based on the count # FA, e.g. whenever the count # FA exceeds a count limit. Alternatively or additionally, the updater 26 may be triggered to generate the control signal C whenever the allowable range ΔL is changed by the operator or the main control unit of the apparatus 1 (cf. VPM technique below). FIG. 4 serves to illustrate an implementation in which the updater 26 generates the control signal C to update the allowable range ΔL used by the analyzer 23. FIG. 4 is a plot of a measurement signal Pi, and dashed vertical lines represent the time points at which the updater 26 updates the allowable range ΔL as a function of the count # FA. The count # FA is produced by the FA analyzer 25 for a preceding time segment Δt in the measurement signal. The time segment Δt may be longer than, equal to or a subset of the time period between consecutive updates. The time segment Δt may be predefined and fixed. Alternatively, the time segment Δt may be intermittently adjusted, e.g. based on the count # FA. The illustration in FIG. 4 is applicable to both the first implementation concept and the second implementation concept as presented above.

In FIG. 4, as well as in all other embodiments described herein, the count # FA is generated to enable a comparison of counts independent of the extent of the time period Δt and is given per unit time, in a broad sense. The count # FA may be obtained by incrementing a counter for each false alarm that is identified during the time period Δt, and by dividing the resulting number by the extent of the time period Δt in any time frame, e.g. seconds, minutes, hours, number of data samples, etc. If the counts to be compared are obtained for time periods Δt of equal extent, the resulting number may be used as the count # FA without normalization by time, since the resulting number is effectively a count per unit time.

Figure 7:
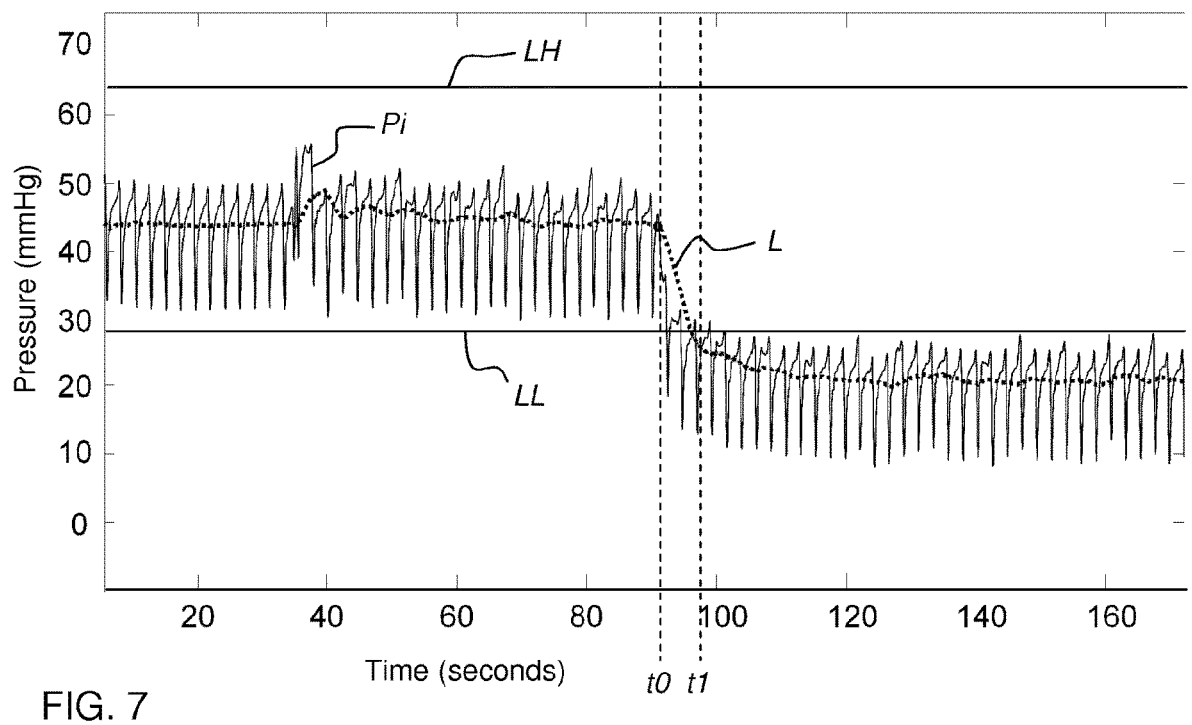
FIG. 7 illustrates VND detection based on pressure level monitoring.

For the purpose of illustration, two types of VND techniques that may be executed by the monitoring device 9 will be briefly exemplified with reference to FIGS. 7-8, in the context of the apparatus as depicted in FIG. 1.

One of the exemplifying VND techniques is conventionally used in dialysis machines and is denoted VPM ("Venous Pressure Monitoring") herein. The VPM technique is based on the principle that a venous-side disruption ("VND event") results in a change in blood pressure measured by the venous sensor 8a. If the access device 2" is detached from the vascular access 3 without changing the vertical position (altitude) of the access device 2", the change in venous pressure is equal to the access pressure, i.e. the pressure in the vascular access 3. This principle is exemplified in FIG. 7, in which a VND event occurs at time point t0. FIG. 7 illustrates the venous signal Pi obtained from the venous pressure sensor 8a. As seen, the venous signal Pi exhibits strong pulsations that originate from the operation of the blood pump 4, in this example a peristaltic pump. To facilitate detection of the pressure change, the venous signal Pi is processed, e.g. by filtering, for extraction of parameter values L that represent the pressure level on the venous side of the EC circuit 1a. The parameter values L are compared to an allowable range which may be defined by a lower limit LL, where an alarm indication is generated at time t1 in FIG. 7, when a count of consecutive parameter values L that fall below the lower limit LL is found to exceed a predefined number limit. To avoid missing an alarm situation when the parameter values L fluctuate around the lower limit LL, a hysteresis may be introduced in the detection by adding a second lower limit (not shown) slightly above the lower limit LL. With such a hysteresis, the counting of consecutive parameter values L may start at the time point when a parameter value is found to fall below the lower limit LL and continue as long as the following consecutive parameter values remain below the second lower limit. As indicated in FIG. 7, an upper limit LH may also be set for detection of malfunctions that cause an increase in venous-side pressure, such as infiltration. Further, the upper limit LH may be set to detect a situation in which the venous-side pressure increases when the access device 2" is detached from the vascular access 3, e.g., if the detached access device 2" gets stuck in the bedclothes or the clothes of the patient or if the detached access device 2" ends up at a higher altitude than the vascular access 3 (thereby increasing the hydrostatic pressure on the venous side). Conventionally, the limits LL, LH are set, automatically by the main control unit of the apparatus 1 or manually by an operator, and subsequently acknowledged by the operator at the beginning of blood treatment and may remain fixed throughout the blood treatment. The apparatus 1 may allow the operator to manually change the limits LL, LH during blood treatment, and the main control unit of the apparatus 1 may automatically change the limits LL, LH when the blood flow in the EC circuit 1a is changed.

With respect to VPM, it has been proposed in U.S. Pat. No. 7,575,562 to adjust the location of the range ΔL with respect to the current signal level in the venous signal at well-defined time intervals, so that the range ΔL follows natural variations in the venous pressure signal while ensuring that a VND event is accurately detected. Similarly, JP2010-136745 proposes to update the location of the range ΔL based on concurrent changes in an arterial signal generated by an arterial pressure sensor in the EC circuit (cf. 8b in FIG. 1).

In the context of VPM, it is also known to generate the parameter values to represent a combination of the venous and arterial signals. For example, US2011/0034814 proposes to generate the parameter values to represent a pressure differential between the venous and arterial signals, for the purpose of reducing the impact of patient movement on the parameter values.

It is realized that the disruption detector 20 of FIG. 2 may be configured to implement the VPM techniques as described in the foregoing.

The other of the VND techniques to be briefly described is denoted PPM ("Pressure Pulse Monitoring") herein and is based on the principle that a venous-side disruption ("VND event") results in a decrease or disappearance in the venous signal of pressure pulsations ("target pulses") that represent pressure waves that have propagated through the fluid connection that is monitored for disruption. The pressure waves may originate from a pulse generator associated with the patient, e.g. a physiological pulse generator PH (FIG. 1) in the patient, such as the heart or the breathing system, or a separate device attached to the patient. Different implementations of the PPM technique are e.g. described in U.S. Pat. No. 6,090,048, WO2009/156174, WO2010/149726, US2005/0010118 and WO2011/080193. In a variant of the PPM technique, proposed in WO2012/175267, the arterial signal is analyzed for detection of target pulses that originate from the blood pump and have propagated through the vascular access to the arterial sensor.

The PPM technique may involve a filtering of the respective pressure signal to suppress interfering signal artifacts, such as pulsations caused by the blood pump, while retaining the target pulses. The resulting monitoring signal is then processed for extraction of parameter values of a detection parameter that represents the magnitude of the target pulses, and the parameter values are compared to an allowable range, as described in relation to FIG. 3. Many different detection parameters are known in the art, e.g. (average) magnitude of pulsations in the monitoring signal, a variability of signal values within a time window in the monitoring signal, a correlation coefficient obtained by the correlating the monitoring signal with a reference signal, a magnitude of a frequency component in a frequency spectrum obtained by frequency analysis of the monitoring signal, etc.

Figure 8A:
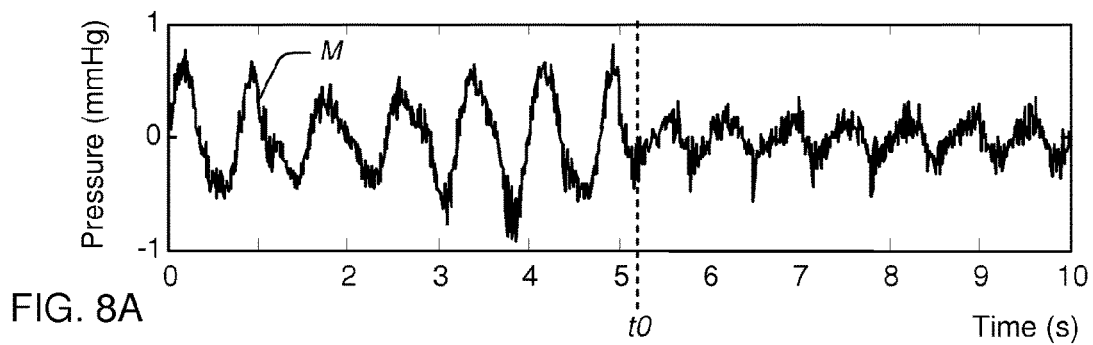
FIGS. 8A-8B illustrate VND detection based on pressure pulsation monitoring.
Figure 8B:
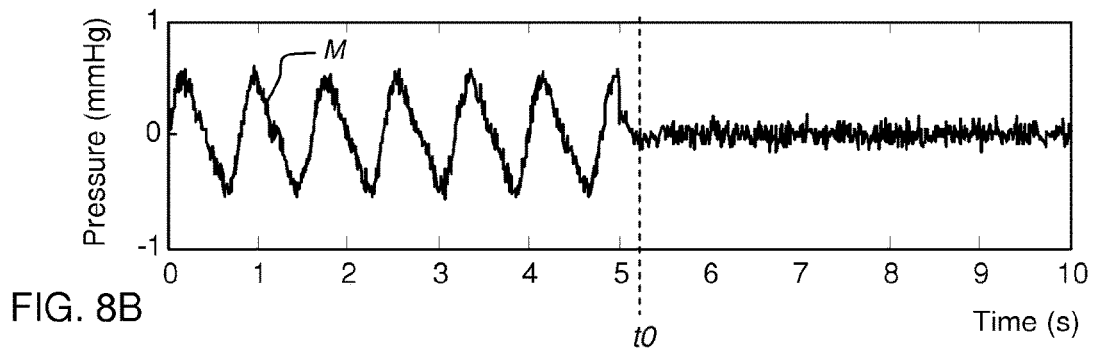

The PPM technique is further exemplified in FIG. 8A, which illustrates a monitoring signal M obtained by filtering a venous signal which is obtained during operation of a blood processing apparatus (cf. 1 in FIG. 1). The monitoring signal M includes target pulses, which disappear at time point t0 when a VND event occurs. As seen in FIG. 8A, weak pulsations remain in the monitoring signal after the VND event. The weak pulsations are residuals of the signal artifacts that are suppressed by the filtering, specifically pulsations originating from the blood pump. FIG. 8B illustrates a corresponding monitoring signal M obtained when the blood pump has been disabled.

It is realized that the disruption detector 20 of FIG. 2 may be configured to implement the PPM technique as described in the foregoing.

Figure 5A:
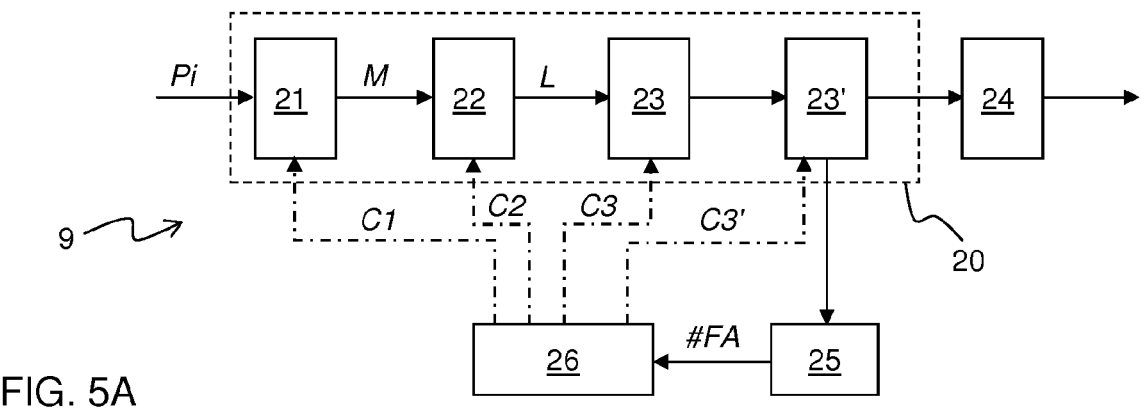
FIG. 5A is a block diagram of a monitoring device according to a first implementation concept.

The first implementation concept will now be exemplified with reference to FIG. 5A, which is a block diagram of a monitoring device 9. For brevity of presentation, the following description will focus on differences compared to the embodiment in FIG. 2. Unless otherwise stated, it can be assumed that the description of FIG. 2 is equally applicable to FIG. 5A.

The disruption detector 20 comprises a validation sub-module 23', which is configured to perform an automatic validation of each alarm indication produced by the analyzer 23. In the validation, the respective alarm indication is classified as "false" or "true", i.e. unlikely to represent a disruption and likely to represent a disruption, respectively. The alarm indications that are classified as true ("true alarm indications") cause the alarm module 24 to generate the alarm signal, whereas the other alarm indications ("false alarm indications" or "false alarms") result in no action by the alarm module 24 and are thus hidden to the user.

The validation sub-module 23' performs the automatic validation by invoking a change to the operation of the apparatus 1 and/or to the operation of the disruption detector 20 and by evaluating the resulting output of the analyzer 23. If the analyzer 23 again produces an alarm indication after this change, the validation sub-module 23' may conclude that the alarm indication is a true alarm indication. The change to the operation of the apparatus 1 may involve intermittently disabling one or more sources of signal interferences in the measurement signal. The change to the operation of the disruption detector 20 may involve causing sub-modules 21-23 to obtain and process another measurement signal from another sensor in the apparatus 1 or on the patient 100 and/or causing the extractor 22 to generate parameter values for another detection parameter as a function of the measurement signal. For example, the validation may involve switching between two different disruption detection techniques (e.g. VPM and PPM) and/or intermittently stopping the blood pump. As understood from FIGS. 8A-8B, the detection of a disappearance of target pulses is facilitated by stopping the blood pump.

The FA analyzer 25 is configured to count the number of false alarms identified by the validation sub-module 23'. The updater 26 is configured to generate, as a function of the count # FA, one or more control signals C1, C2, C3 for updating the respective sub-module 21, 22, 23, e.g. as described in relation to FIG. 2. The updater 26 may also be configured to generate a control signal C3' for updating the validation sub-module 23', e.g. to activate/deactivate the automatic validation.

Figure 5B:
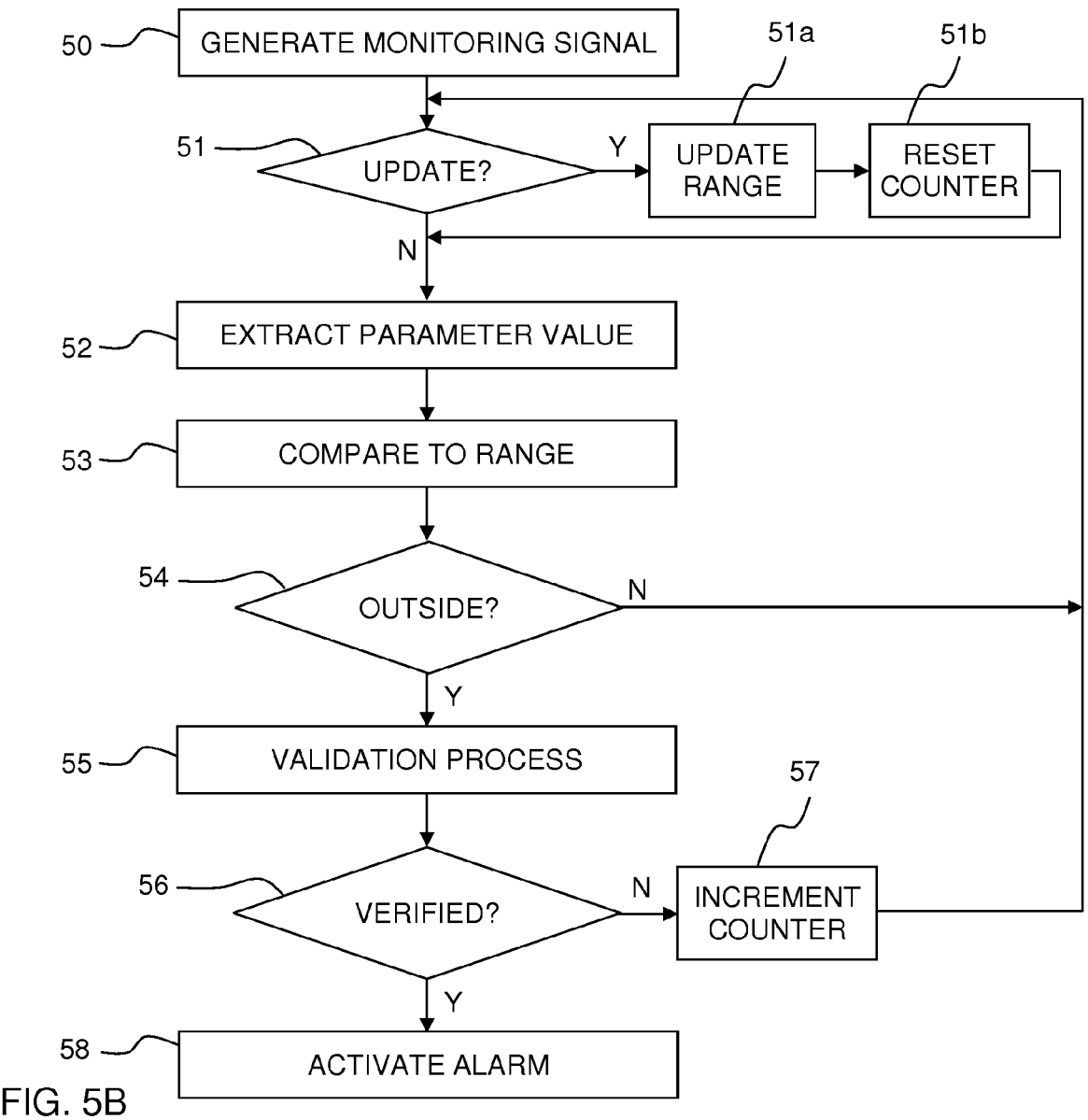
FIG. 5B is a flow chart of a monitoring process executed by the monitoring device of FIG. 5A.

An example of the operation of the monitoring device 9 in FIG. 5A is given in the flow chart of FIG. 5B. The illustrated example presumes that the updater 26 generates the control signal C3 to update the range ΔL used by the analyzer 23. The monitoring process in FIG. 5B involves a step 50 of generating the monitoring signal M. Typically, step 50 operates continuously to generate a sequence of signal values at a fixed or variable rate while the process repeatedly proceeds through steps 51-57 to detect a disruption based on the signal values. Step 51 determines if an update of the range ΔL should be initiated. Step 51 may e.g. initiate the update at given time intervals or if the current count of false alarms exceeds a count limit. If no update is due, the process proceeds to step 52 which extracts a parameter value from the monitoring signal M. Step 53 compares the parameter value to the current range ΔL. If the parameter value falls outside the current range ΔL, step 54 generates an alarm indication and proceeds to step 55 which initiates the automatic validation. Otherwise, step 54 proceeds to step 51. Step 54 may apply an additional detection criterion before proceeding to step 55, e.g. that a predefined number of consecutive parameter values fall outside the current range ΔL or that a predefined number parameter values within a given time period fall outside the current range ΔL. If the alarm indication is not verified as true by the automatic validation, step 56 directs the process to step 57, which increments a counter of false alarms (which is set to zero at startup of the process), and then to step 51. If the alarm indication is verified, step 56 directs the process to step 58, which generates the alarm signal. If an update is due in step 51, the process executes step 51a which updates the range ΔL based on the current setting of the counter. Step 51a may e.g. increase or decrease the range as a function of the number of false alarms, by shifting at least one of the limits LL, LH. After step 51a, the counter is reset to zero in step 51b and the process proceeds to step 52.

In the context of FIG. 5A, step 50 is executed by module 21, step 52 is executed by module 22, steps 53-54 are executed by module 23, steps 55-56 are executed by module 23', step 58 is executed by module 24, step 57 and 51b are executed by module 25, and steps 51, 51a are executed by module 26.

The monitoring process in FIG. 5B may update the range ΔL in different ways. In a first example, the process starts from a wide range ΔL, which may be entered by an operator or be a default range stored in the monitoring device, and then gradually decreases the range ΔL for each execution of step 51a, until a desired count of false alarms per unit time is obtained. The process then operates step 51a to update the range ΔL so as to essentially maintain the desired count of false alarms per unit time. In a second example, which may be preferable if the desired count of false alarms per unit time is very low, e.g. 1 or 2 per hour, the process intermittently executes a probing in which the current range ΔL is gradually decreased by step 51a at relatively small time intervals, e.g. every 1-10 minutes, until the count of false alarms during the time interval reaches a given value, e.g. 1-10. The range ΔL is then increased by a predefined amount. The predefined amount may be obtained by testing to approximately yield the desired number of false alarms per unit time. The range ΔL may then be maintained for a given period, e.g. 15-60 minutes, before the method again executes the probing, and so on.

Figure 6A:
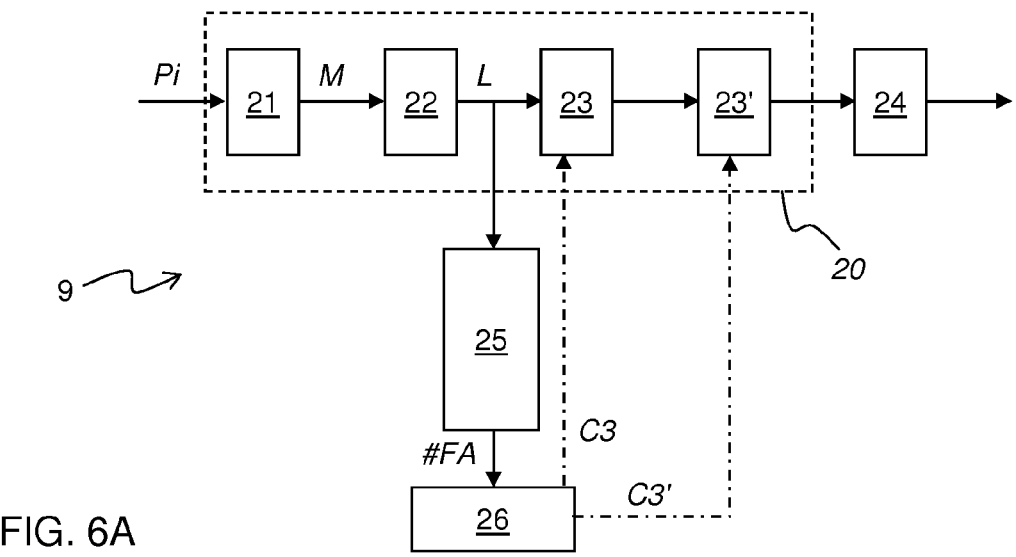
FIG. 6A is a block diagram of a monitoring device according to a second implementation concept.

The second implementation concept will now be exemplified with reference to FIG. 6A, which is a block diagram of a monitoring device 9. For brevity of presentation, the following description will focus on differences compared to the embodiment in FIG. 2. Unless otherwise stated, it can be assumed that the description of FIG. 2 is equally applicable to FIG. 6A.

In the illustrated example, the disruption detector 20 comprises a validation sub-module 23', which may be identical to the validation sub-module 23' in FIG. 5A. However, it should be noted that the FA analyzer 25 in FIG. 6A operates independently of the false alarms identified by the validation sub-module 23'. Thus, the validation sub-module 23' is optional, as will be further discussed below. The FA analyzer 25 is configured to obtain a time-sequence of parameter values L from the extractor 22. The parameter values correspond to a time segment in the measurement signal (cf. At in FIG. 4). The FA analyzer 25 is further configured to estimate the number of false alarms that would be generated for the time-sequence of parameter values L by the disruption detector 20 in different configurations. Thus, the FA analyzer 25 produces one count for each configuration, without actually operating the disruption detector 20 in any of these different configurations. The updater 26 is configured to update the disruption detector 20 based on the count produced by the FA analyzer 25, e.g. by setting the disruption detector 20 in the configuration that is found to produce a desired number of counts.

It may be noted in FIG. 6A, that the updater 26 is only operable to generate control signals C3, C3' for updating the sub-modules 23, 23' since only modifications to the configuration of these sub-modules can be evaluated by the FA analyzer 25. In a variant (not shown), the module 25 obtains the monitoring signal M from module 21, and thereby enables the updater 26 to update one or more of sub-modules 22, 23, 23'. In a further variant (not shown), the FA analyzer 25 obtains the measurement signal Pi, and thereby enables the updater 26 to update one or more of sub-modules 21, 22, 23, 23'.

As noted above, the validation sub-module 23' is optional. In the absence of the validation sub-module 23', all alarm indications produced by the analyzer 23 will cause the alarm module 24 generate the alarm signal and thus call for the attention of an operator. It may therefore be preferable to set the desired count for the updater 26 to a small number per unit time. Conversely, the provision of the validation sub-module 23' effectively prevents false alarms from causing alarm signals and thus allows the desired count to be set to a larger number per unit time.

Figure 6B:
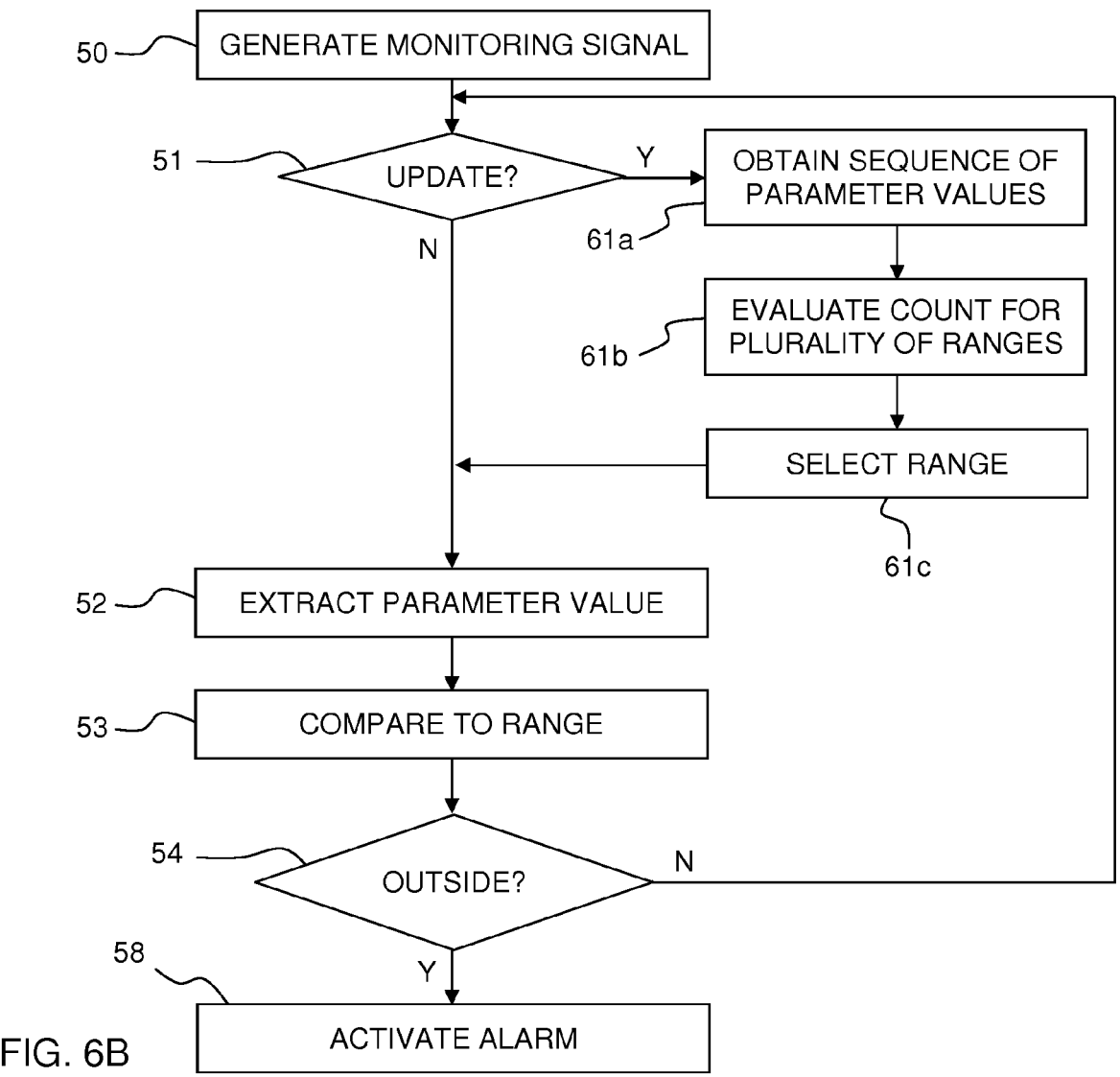
FIG. 6B is a flow chart of a monitoring process executed by the monitoring device of FIG. 6A.

An example of the operation of the monitoring device 9 in FIG. 6A is given in the flow chart of FIG. 6B. The illustrated example presumes that the updater 26 generates the control signal C3 to update the range ΔL used by the analyzer 23, and that the validation sub-module 23' is omitted or disabled. Many steps of the monitoring process in FIG. 6B are identical to steps of the monitoring process in FIG. 5B and are designated by the same reference numerals. The description of these steps will not be reiterated. Instead, attention is given to steps 61a, 61b, 61c which are executed if an update is due in step 51. Step 61a obtains a sequence of parameter values, which have previously been generated by executions of step 52. For example, step 52 may store each parameter value in memory (cf. 12 in FIG. 1) for later retrieval by step 61a. Step 61b compares each parameter value in the sequence of parameter values to a plurality of different ranges ("test ranges"). Whenever a parameter value falls outside a test range, step 61b increments a counter for the test range, thereby producing a count of false alarms for each test range. Step 61c may then set the current range to be used by step 53 as a function of the test range for which the count meets a desired value. In a variant of the monitoring process in FIG. 6B, step 61a is omitted and step 61b is executed subsequent to step 52 and modified to compare the individual parameter value generated by step 52 to the test ranges and to selectively increment the counters for the test ranges based on the comparison. When an update is due in step 51, step 61c is executed to retrieve the current count for each test range and use this information to set the current range for use by step 53.

In the context of FIG. 6A, step 50 is executed by module 21, step 52 is executed by module 22, steps 53-54 are executed by module 23, step 58 is executed by module 24, steps 61a, 61b are executed by module 25, and steps 51, 61c are executed by module 26.

In all embodiments and implementations disclosed herein, the analyzer 23 (and step 53) may compare the parameter values to one or more additional alarm limits that are fixed throughout the monitoring process, or at least are not updated by the updater 26 (and steps 51a, 61c). Such "global" alarm limits may be predefined or set by the operator or by the apparatus 1 at the start of a blood treatment. The analyzer 23 (and step 54) may declare a malfunction if a predefined number of parameter values fall outside such a global alarm limit, causing the alarm device 24 (and step 58) to generate the alarm signal. In the context of VPM techniques, a global alarm limit may be set to detect malfunctions that result in a slow trend of pressure increase or decrease in the time-sequence of parameter values L. Such malfunctions may include a gradual clogging of the access device 2" that results in a slow increase in the venous-side pressure in the EC circuit 1a, or a small, but growing, blood leakage in the EC circuit 1a (e.g. at the connection of the access device 2" to the vascular access 3) that results in a gradual decrease in the blood pressure of the patient, and hence the access pressure and thereby the venous-side pressure in the EC circuit 1a.

In all embodiments and implementations disclosed herein, the updating of the disruption detection 20 may be combined with any technique that adjusts the location of the range ΔL, e.g. as described hereinabove with reference to known VPM techniques.

The monitoring device 9 as described herein may be implemented by special-purpose software (or firmware) run on one or more general-purpose or special-purpose computing devices. In this context, it is to be understood that a "module" or "means" of such a computing device refers to a conceptual equivalent of a method step; there is not always a one-to-one correspondence between modules/means and particular pieces of hardware or software routines. One piece of hardware sometimes comprises different modules/means. For example, a processing unit serves as one module/means when executing one instruction, but serves as another module/means when executing another instruction. In addition, one module/means may be implemented by one instruction in some cases, but by a plurality of instructions in some other cases. Such a software controlled computing device may include one or more processing units (cf. 11 in FIG. 1), e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The device 9 may further include a system memory (cf. 12 in FIG. 1) and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The device 9 may include one or more communication interfaces (cf. 10 in FIG. 1), such as a serial interface, a parallel interface, a USB interface, a wireless interface, a network adapter, etc, as well as one or more data acquisition devices, such as an A/D converter. The special-purpose software may be provided to the device 9 on any suitable computer-readable medium, transitory or non-transitory, including a record medium or a read-only memory.

It is also conceivable that some (or all) elements/means are fully or partially implemented by dedicated hardware, such as an FPGA, an ASIC, or an assembly of discrete electronic components (resistors, capacitors, operational amplifier, transistors, filters, etc), as is well-known in the art.

It should be emphasized that the invention is not limited to digital signal processing, but could be fully implemented by a combination of analog devices.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, it is to be understood that the first and second implementation concepts may be combined.

Further, the inventive monitoring is applicable to fluid systems that contain other liquids than blood and are connected to the cardiovascular system of a human or animal subject, including systems for intravenous therapy, infusion systems, automated peritoneal dialysis (APD) systems, etc. Examples of such liquids include medical solutions, dialysis fluids, infusion liquids, water, etc.

It should be emphasized that the fluid containing systems need not involve a human or animal subject. For example, the inventive monitoring technique may be used to detect a disruption of a fluid connection between two machines or between a machine and a container.

The inventive monitoring need not operate on real-time data, but could be used for processing off-line data, such as a previously recorded measurement signal.

The invention claimed is:

1. A monitoring device, comprising:
    a disruption detector configured to obtain a measurement signal, which is generated by a sensor arranged in or associated with a first fluid containing system and is responsive to a disruption of a fluid connection between the first fluid containing system and a second fluid containing system, the disruption detector being further configured to operate on the measurement signal to detect an apparent disruption of the fluid connection and generate an alarm indication corresponding to the apparent disruption;

an alarm module for activating an alarm based on the alarm indication;

a false alarm analyzer configured to produce a count of false alarm indications generated per unit time by the disruption detector for one or more configurations of the disruption detector; and an updater configured to update the configuration of the disruption detector based on the count.

2. The monitoring device of claim 1, wherein the disruption detector is configured to, when operating on the measurement signal, generate a time-sequence of parameter values of a detection parameter to represent a time segment in the measurement signal, compare the time-sequence of parameter values to a current allowable range, and generate the alarm indication when a predefined number of parameter values in the time-sequence of parameter values fall outside the current allowable range.

3. The monitoring device of claim 2, wherein the updater is configured to update the configuration of the disruption detector by one or more of: causing the disruption detector to operate on another measurement signal, causing the disruption detector to modify a preprocessing of the measurement signal, causing the disruption detector to generate the time-sequence of parameter values of another detection parameter, changing the current allowable range, and changing the predefined number of parameter values.

4. The monitoring device of claim 1, wherein the false alarm analyzer is configured to produce the count by estimating, based on the measurement signal, a respective number of false alarm indications generated by the disruption detector for each of a plurality of different configurations of the disruption detector.

5. The monitoring device of claim 1, wherein the false alarm analyzer is configured to compare at least part of a time-sequence of parameter values to an allowable range among a plurality of allowable ranges, identify a respective false alarm indication when a set of parameter values in the time-sequence of parameter values falls outside a respective allowable range, and produce the count to represent the number of false alarm indications for the respective allowable range.

6. The monitoring device of claim 5, wherein the updater is configured to set a current allowable range as a function of the allowable range for which the count meets a desired value.

7. The monitoring device of claim 6, wherein the updater is configured to update the configuration of the disruption detector by increasing or decreasing the current allowable range as a function of the count.

8. The monitoring device of claim 7, wherein the updater is configured to update the configuration of the disruption detector by repeatedly increasing or decreasing the current allowable range until the count meets a desired value.

9. The monitoring device of any one of claim 1, wherein the false alarm analyzer is configured to produce the count to represent the number of false alarm indications among the alarm indications that are generated by the disruption detector over a time period.

10. The monitoring device of claim 1, wherein the disruption detector is further configured to, when operating on the measurement signal, perform an automatic validation of each alarm indication to identify the alarm indication as a false alarm indication or a true alarm indication, wherein the false alarm analyzer is configured to produce the count based on the false alarm indications identified by the automatic validation.

11. The monitoring device of claim 10, wherein the automatic validation involves one or more of: obtaining and processing a further measurement signal generated by a further sensor arranged in or associated with the first or second fluid containing systems and being responsive to the disruption; generating parameter values of another detection parameter as a function of the measurement signal; and intermittently disabling one or more sources of signal interferences in the measurement signal.

12. The monitoring device of claim 10, wherein the first fluid containing system comprises a blood processing apparatus for connection, by the fluid connection, to a subject, wherein the sensor comprises a pressure sensor for sensing a pressure of blood in the blood processing apparatus, wherein the automatic validation comprises: obtaining and processing the measurement signal for detection of pulsations originating from a pulse generator in or associated with the subject.

13. The monitoring device of claim 12, wherein the automatic validation further comprises, before obtaining and processing the measurement signal, generating a control signal to stop one or more pumping device arranged in the blood processing apparatus.

14. The monitoring device of claim 10, wherein the alarm module is configured to activate the alarm signal when the automatic validation identifies the alarm indication as a true alarm indication.

15. The monitoring device of claim 1, wherein the updater is configured to update the configuration of the disruption detector at fixed time intervals and/or triggered by the count.

16. The monitoring device of claim 1, wherein the measurement signal represents fluid pressure in the first fluid containing system, and wherein the parameter values are indicative of one of a pressure level in the first fluid containing system, and pulsations originating from a pulse generator in the second fluid containing system.

17. An apparatus for extracorporeal blood processing, comprising:

an extracorporeal blood circuit for connection to the vascular system of a patient at first and second ends and comprising a blood pump for circulating blood from the first end through a blood processing device to the second end;

a sensor configured to generate a measurement signal which is responsive to a disconnection of the extracorporeal blood circuit from the vascular system of the patient downstream of the blood pump;

a disconnection detector configured to operate the measurement signal for detecting the disconnection and generate an alarm indication corresponding to the disconnection;

an alarm module for activating an alarm based on the alarm indication;

a false alarm analyzer configured to produce a count of false alarm indications generated by the disconnection detector per unit time for one or more configuration of the disconnection detector; and an updater configured to update the configuration of the disconnection detector based on the count.

18. A method of controlling a monitoring device comprising a processor, said method being executed by the processor in the monitoring device and comprising:

obtaining a measurement signal generated by a sensor in a first fluid containing system and being responsive to disruptions of a fluid connection between the first fluid containing system and a second fluid containing system;

operating a detection logic on the measurement signal to detect an apparent disruption of the fluid connection and to generate an alarm indication corresponding to the apparent disruption;

activating an alarm based on the alarm indication; and updating the detection logic based on a count of false alarm indications per unit time among the alarm indications generated by the detection logic for one or more configuration of the detection logic.

19. The method of claim 18, further comprising: estimating, based on the measurement signal, the number of false alarm indications generated by the detection logic for each of a plurality of different configurations of the detection logic, and producing the count to represent the number of false alarm indications for each of the plurality of different configurations.

20. The method of claim 18, further comprising: producing the count to represent the number of false alarm indications per unit time among the alarm indications that are generated when operating the detection logic, in a current configuration, on the measurement signal.

21. A computer-readable medium comprising processing instructions for causing a data processor to perform the method of claim 18.

* * * * *